United States Patent
Varga et al.

(10) Patent No.: US 9,272,113 B2
(45) Date of Patent: Mar. 1, 2016

(54) TRANSPORTING LIQUID IN A RESPIRATORY COMPONENT

(75) Inventors: Christopher M. Varga, Laguna Hills, CA (US); Neil Korneff, Diamond Bar, CA (US)

(73) Assignee: CareFusion 207, Inc., San Diego, CA (US)

( * ) Notice: Subject to any disclaimer, the term of this patent is extended or adjusted under 35 U.S.C. 154(b) by 254 days.

(21) Appl. No.: 13/436,775

(22) Filed: Mar. 30, 2012

(65) Prior Publication Data

US 2013/0255672 A1  Oct. 3, 2013

(51) Int. Cl.
| | |
|---|---|
| *A61M 16/00* | (2006.01) |
| *A62B 7/00* | (2006.01) |
| *F24J 3/00* | (2006.01) |
| *A61M 16/08* | (2006.01) |
| *A61M 16/10* | (2006.01) |
| *A61M 16/04* | (2006.01) |
| *A61M 16/06* | (2006.01) |
| *A61M 16/16* | (2006.01) |
| *A61M 11/00* | (2006.01) |

(52) U.S. Cl.
CPC ........... *A61M 16/0808* (2013.01); *A61M 16/08* (2013.01); *A61M 16/105* (2013.01); *A61M 16/1045* (2013.01); *A61M 16/1075* (2013.01); *A61M 11/00* (2013.01); *A61M 16/04* (2013.01); *A61M 16/0465* (2013.01); *A61M 16/06* (2013.01); *A61M 16/0666* (2013.01); *A61M 16/0875* (2013.01); *A61M 16/1095* (2014.02); *A61M 16/16* (2013.01); *A61M 2205/0227* (2013.01); *A61M 2205/18* (2013.01); *A61M 2205/7527* (2013.01); *A61M 2207/00* (2013.01)

(58) Field of Classification Search
CPC ............................ A61M 16/0808; A61M 16/08
USPC .................. 128/200.24, 203.16–203.17, 128/203.26–203.27, 204.13, 204.17, 128/205.27, 205.12, 206.22
See application file for complete search history.

(56) References Cited

U.S. PATENT DOCUMENTS

| | | |
|---|---|---|
| 2,256,991 A | 9/1941 | Sabins |
| 3,811,496 A | 5/1974 | Asselman et al. |
| 3,893,458 A | 7/1975 | Fletcher et al. |
| 4,013,742 A | 3/1977 | Lang |
| 4,098,853 A | 7/1978 | Brown et al. |
| 4,216,176 A | 8/1980 | Tanaka |
| 4,303,601 A | 12/1981 | Grimm et al. |
| 4,354,984 A | 10/1982 | Richardson et al. |

(Continued)

FOREIGN PATENT DOCUMENTS

| | | |
|---|---|---|
| DE | 10016005 A1 | 12/2001 |
| EP | 1671668 A1 | 6/2006 |

(Continued)

OTHER PUBLICATIONS

International Search Report and Written Opinion for PCT/US2013/033946 mailed Jul. 18, 2013.

(Continued)

*Primary Examiner* — Kristen Matter
(74) *Attorney, Agent, or Firm* — McDermott Will & Emery LLP

(57) ABSTRACT

A respiratory component coupled with a breathing circuit, the respiratory component including at least one groove disposed upon a surface of the respiratory component, wherein the respiratory component is not a heater wire.

22 Claims, 9 Drawing Sheets

(56) References Cited

U.S. PATENT DOCUMENTS

| | | | |
|---|---|---|---|
| 4,386,582 A | 6/1983 | Adsit | |
| 4,441,027 A | 4/1984 | Richardson et al. | |
| 4,630,475 A | 12/1986 | Mizoguchi | |
| 4,644,790 A | 2/1987 | Mizoguchi | |
| 4,682,010 A | 7/1987 | Drapeau et al. | |
| 4,921,642 A | 5/1990 | LaTorraca | |
| 5,052,476 A * | 10/1991 | Sukumoda et al. | 165/133 |
| 5,195,515 A | 3/1993 | Levine | |
| 5,231,979 A | 8/1993 | Rose et al. | |
| 5,286,942 A | 2/1994 | McFadden et al. | |
| 5,373,841 A | 12/1994 | Kyllonen et al. | |
| 5,383,574 A | 1/1995 | Raphael | |
| 5,438,233 A | 8/1995 | Boland et al. | |
| 5,577,494 A * | 11/1996 | Kuypers et al. | 128/201.13 |
| 5,586,214 A | 12/1996 | Eckman | |
| 5,640,951 A | 6/1997 | Huddart et al. | |
| 6,167,883 B1 | 1/2001 | Beran et al. | |
| 6,272,933 B1 | 8/2001 | Gradon et al. | |
| 6,335,517 B1 | 1/2002 | Chauviaux et al. | |
| 6,349,722 B1 | 2/2002 | Gradon et al. | |
| 6,584,972 B2 | 7/2003 | McPhee | |
| 6,694,974 B1 | 2/2004 | George-Gradon et al. | |
| 6,766,817 B2 | 7/2004 | da Silva | |
| 6,802,314 B2 | 10/2004 | McPhee | |
| 6,804,656 B1 | 10/2004 | Rosenfeld et al. | |
| 6,918,389 B2 | 7/2005 | Seakins et al. | |
| 7,043,979 B2 | 5/2006 | Smith et al. | |
| 7,051,733 B2 | 5/2006 | Gradon et al. | |
| 7,207,945 B2 | 4/2007 | Bardy | |
| 7,263,994 B2 | 9/2007 | Gradon et al. | |
| 7,559,324 B2 | 7/2009 | Smith et al. | |
| 7,637,287 B2 | 12/2009 | Reinhard et al. | |
| 7,651,542 B2 | 1/2010 | Shurtleff et al. | |
| 7,959,574 B2 | 6/2011 | Bardy | |
| 8,037,882 B2 | 10/2011 | Smith et al. | |
| 8,578,789 B2 | 11/2013 | Murata | |
| 8,733,348 B2 | 5/2014 | Korneff et al. | |
| 2004/0016430 A1 | 1/2004 | Makinson et al. | |
| 2004/0221844 A1 | 11/2004 | Hunt et al. | |
| 2005/0139211 A1* | 6/2005 | Alston et al. | 128/200.14 |
| 2006/0124127 A1* | 6/2006 | Du et al. | 128/201.13 |
| 2006/0278222 A1 | 12/2006 | Schermeier et al. | |
| 2007/0107801 A1 | 5/2007 | Cochran et al. | |
| 2007/0144519 A1 | 6/2007 | Henry et al. | |
| 2008/0035154 A1* | 2/2008 | Johnson | 128/207.14 |
| 2008/0066751 A1 | 3/2008 | Polacsek | |
| 2008/0072904 A1 | 3/2008 | Becker et al. | |
| 2008/0078386 A1 | 4/2008 | Feldhahn et al. | |
| 2008/0190427 A1 | 8/2008 | Payton et al. | |
| 2009/0000620 A1 | 1/2009 | Virr | |
| 2009/0025723 A1 | 1/2009 | Schobel et al. | |
| 2009/0159079 A1 | 6/2009 | Meier | |
| 2009/0173344 A1 | 7/2009 | Short | |
| 2009/0301482 A1 | 12/2009 | Burton et al. | |
| 2010/0044267 A1 | 2/2010 | Tolibas-Spurlock et al. | |
| 2010/0083965 A1 | 4/2010 | Virr et al. | |
| 2010/0132708 A1 | 6/2010 | Martin et al. | |
| 2010/0230503 A1 | 9/2010 | Nakaguro | |
| 2011/0023874 A1 | 2/2011 | Bath et al. | |
| 2011/0120462 A1 | 5/2011 | Tatkov et al. | |
| 2011/0253136 A1 | 10/2011 | Sweeney et al. | |
| 2011/0265024 A1 | 10/2011 | Leone et al. | |
| 2012/0167880 A1 | 7/2012 | Jacob | |
| 2012/0227738 A1 | 9/2012 | Virr et al. | |
| 2013/0031620 A1 | 1/2013 | Fascenda | |
| 2013/0081582 A1 | 4/2013 | Varga | |
| 2013/0081618 A1 | 4/2013 | Korneff et al. | |
| 2013/0081620 A1 | 4/2013 | Korneff et al. | |
| 2013/0081621 A1 | 4/2013 | Korneff et al. | |
| 2013/0081622 A1 | 4/2013 | Korneff et al. | |
| 2013/0081625 A1 | 4/2013 | Rustad et al. | |
| 2013/0081701 A1 | 4/2013 | Korneff et al. | |
| 2014/0251331 A1 | 9/2014 | Korneff et al. | |

FOREIGN PATENT DOCUMENTS

| | | |
|---|---|---|
| JP | 05285220 B2 | 11/1993 |
| JP | 07219650 | 8/1995 |
| WO | 9718001 A1 | 5/1997 |
| WO | WO-03055553 A | 7/2003 |
| WO | WO-2004105848 A1 | 12/2004 |
| WO | WO-2008095245 A1 | 8/2008 |

OTHER PUBLICATIONS

International Search Report in PCT Application No. PCT/US2013/033946 dated Oct. 3, 2013.
Written Opinion of the International Searching Authority in PCT Application No. PCT/US2013/033946 dated Jul. 18, 2013.
International Preliminary Report on Patentability in PCT Application No. PCT/US2013/033946 dated Oct. 1, 2014.
European Office Action for European Application No. 12835170, dated Mar. 20, 2015, 4 pages.
Extended European Search Report for European Application No. 12835170, dated Mar. 3, 2015, 3 pages.
International Preliminary Report on Patentability for International Application No. PCT/US2012/058043, dated Apr. 1, 2014, 8pages.
International Search Report and Written Opinion for International Application No. PCT/US2012/058043, dated Mar. 25, 2013, 13 pages.
European Partial Supplementary Search Report for Application No. 13769160.6, dated Sep. 7, 2015, 8 pages.

* cited by examiner

TRANSPORTING LIQUID IN A RESPIRATORY COMPONENT

CROSS REFERENCE TO RELATED APPLICATIONS

This application is related to U.S. patent application Ser. No. 13/250,894 entitled FLUTED HEATER WIRE, by Neil Korneff et al., assigned to the assignee of the present invention, filed Sep. 30, 2011.

FIELD OF THE INVENTION

The present technology relates generally to the respiratory field. More particularly, the present technology relates to humidification.

BACKGROUND

Respiratory humidification systems are used in providing respiratory therapy to a patient. In general terms, the system includes a ventilator, humidifier and patient circuit. The ventilator supplies gases to a humidification chamber coupled with the humidifier. Water within the humidification chamber is heated by the humidifier, which produces water vapor that humidifies gases within the chamber. From the chamber, humidified gases are then carried to the patient through the patient circuit.

DESCRIPTION OF EMBODIMENTS

The drawings referred to in this description should not be understood as being drawn to scale unless specifically noted.

DESCRIPTION OF EMBODIMENTS

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope. Furthermore, in the following description, numerous specific details are set forth in order to provide a thorough understanding of the subject matter. However, some embodiments may be practiced without these specific details. In other instances, well-known structures and components have not been described in detail as not to unnecessarily obscure aspects of the subject matter.

Overview of Discussion

Herein, various embodiments of a humidification component and methods for providing respiratory therapy to a patient are described. The description begins with a brief general discussion of traditional humidification systems. This general discussion provides a framework of understanding for more a particularized description which follows, focusing on particular features and concepts of operation associated with one or more embodiments of the described humidifier technology.

Humidification Systems

Traditional humidification systems for respiratory gas delivery in critical care and patient care settings typically involve a chamber of hot water which is used to provide vapor for humidifying the delivered gases. The method for heating this water bath is most often contact heating using a hot-plate or heating element which transfers heat to the water through a metallic surface which is incorporated into the humidification chamber.

Embodiments provide a method and device for at least one or more of the following: transporting liquid in a respiratory component from a first location to a second location; removing condensation from a humidification component; moving liquid (from condensation regions) to heated (hotter) regions for evaporation; moving liquid (from condensation regions) to regions for indication (e.g. indication by chemical reaction); and creating additional surface area for evaporation of liquids to address the problem associated with humidifying liquids within a small volume.

Of note, in one embodiment the humidification component described herein is a structure that retains a fluid therein for humidifying. However, in another embodiment, the humidification component described herein simply refers to the presence of moisture provided.

Figure 6:
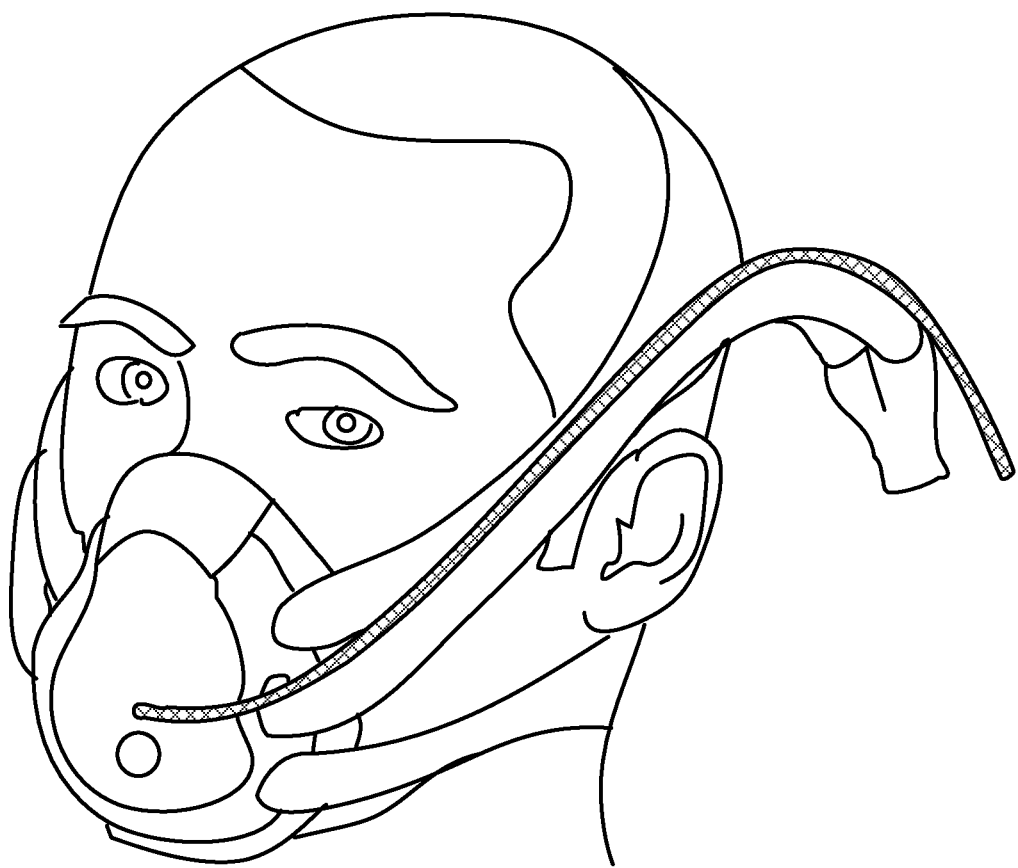
FIG. 6 shows a front perspective view of a patient breathing through a respiratory mask through the upper airways.
Figure 7:
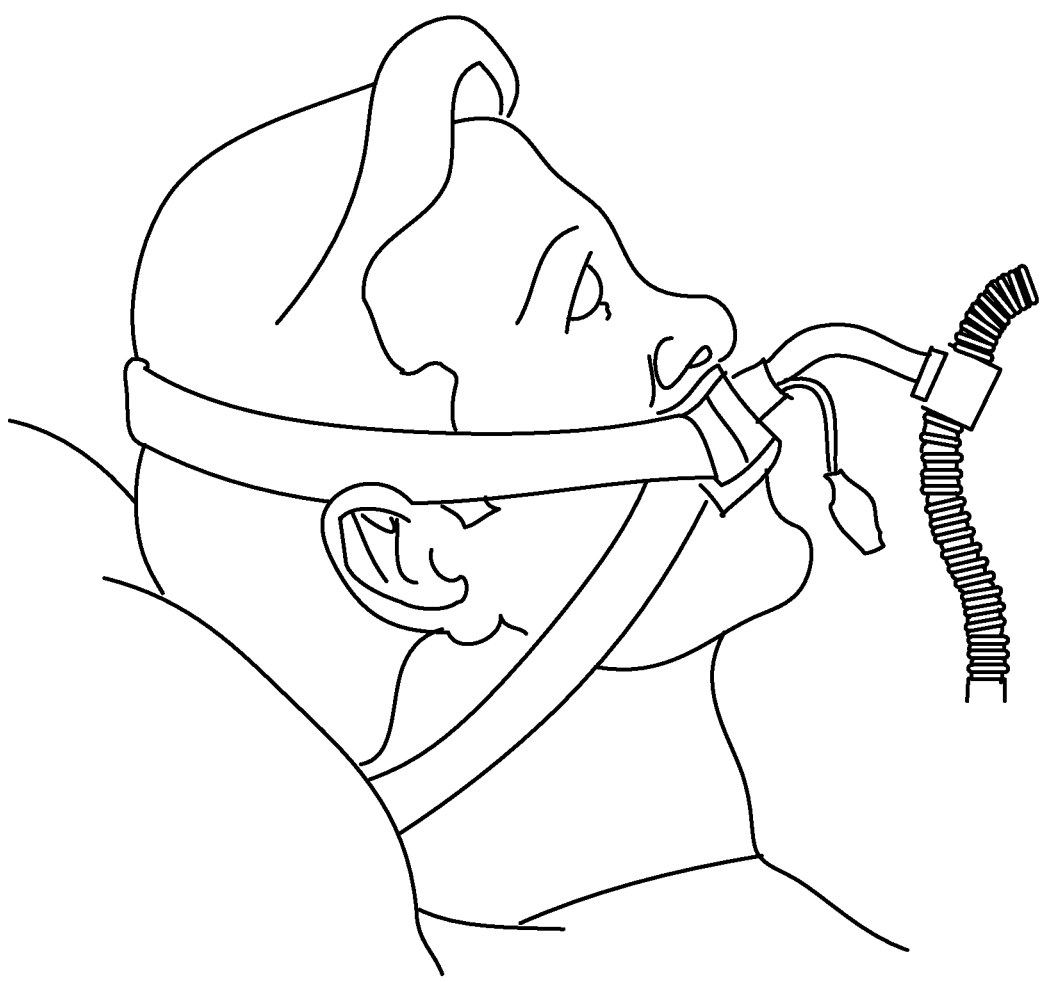
FIG. 7 shows a patient breathing with an endotracheal tube, wherein the patient's upper airways are bypassed.

Furthermore, it should be noted that the methods and devices described herein may be used in various modes of respiratory care, including, but not limited to, non-invasive single limb ventilation, dual-limb invasive ventilation, dual-limb non-invasive ventilation, continuous positive airway pressure (CPAP), bubble CPAP, bi-level positive airway pressure (BiPAP), intermittent positive pressure (IPPB), bland aerosol therapy and oxygen therapy. In general, non-invasive single and dual-limb ventilation refers to the delivery of ventilator support using a mechanical ventilator, with one or multiple limbs, connected to a mask or mouthpiece instead of an endotracheal tube. For example, FIG. 6 shows a front perspective view of a patient breathing with a mask through the upper airways (using a non-invasive ventilation system). A dual-limb invasive therapy refers to the delivery of ventilator support using a mechanical ventilator, with multiple limbs, connected to an endotracheal tube or tracheostomy interface. For example, FIG. 7 illustrates a patient breathing with an endotracheal tube, wherein the patient's upper airways are bypassed (using an invasive ventilation system).

Figure 8:
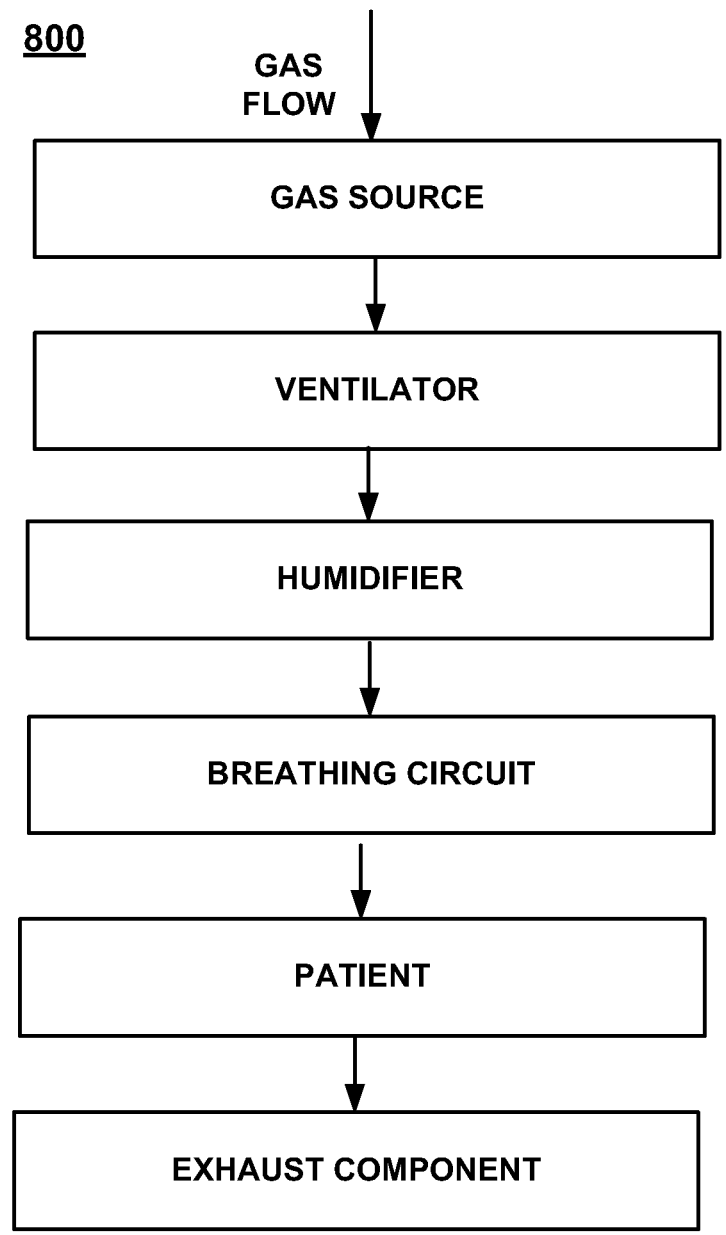
FIG. 8 shows a flow diagram of a flow of gas during single limb ventilation.
Figure 9:
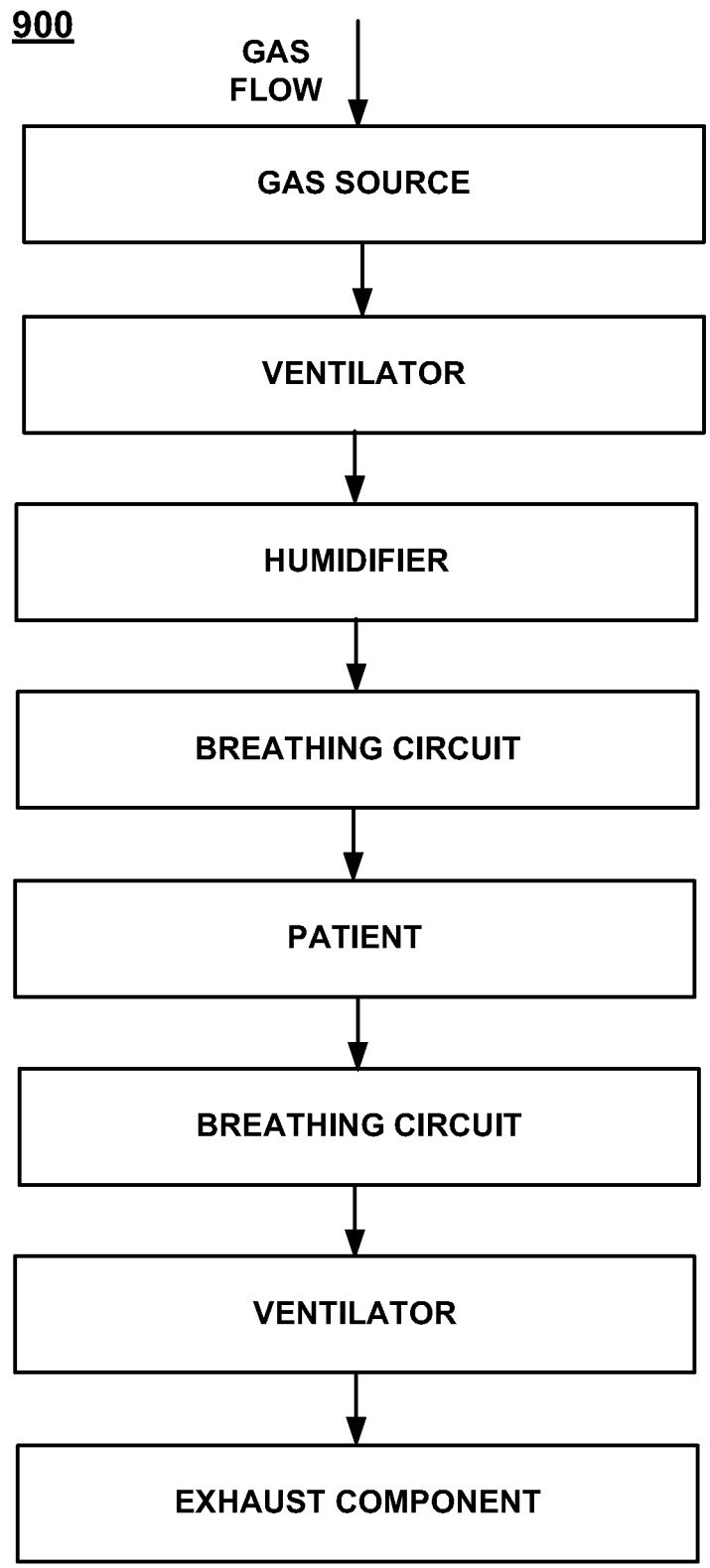
FIG. 9 shows a flow diagram of a flow of gas during dual limb ventilation.

Further, FIGS. 8 and 9 illustrate flow diagrams 800 and 900, respectively, of the flow of gas during single limb and dual limb ventilation, respectively. More particular, 800 of FIG. 8, with regards to single limb ventilation, shows gas flowing from a gas source to a ventilator, to a humidifier, to a breathing circuit, to a patient, to an exhaust component. In contrast, 900 of FIG. 9, with regards to dual limb ventilation, shows gas flowing from a gas source to a ventilator, to a humidifier, to a breathing circuit, to a patient, to a breathing circuit, to a ventilator, to an exhaust component.

CPAP refers to the maintenance of positive pressure in the airway throughout a respiratory cycle. Bubble CPAP refers to a procedure that doctors use to help promote breathing in premature newborns. In bubble CPAP, positive airway pressure is maintained by placing the expiratory limb of the circuit under water. The production of bubbles under the water produces a slight oscillation in the pressure waveform. BiPAP refers to the maintenance of positive pressure during inspiration, but the reduction of positive pressure during expiration. IPPB refers to the non-continuous application of positive airway pressure when, for example, an episode of apnea is sensed. Bland aerosol therapy refers to the delivery of hypotonic, hypertonic, or isotonic saline, or sterile water in aerosolized form, to a patient as a medical intervention. Oxygen therapy refers to the delivery of oxygen to a patient, as a medical intervention.

The following discussion describes the architecture and operation of embodiments.

Breathing circuits are utilized to deliver such medical support as air and anesthetics from a machine that creates an artificial environment to a patient via tubes. Breathing circuits are used in surgical procedures, respiratory support and respiratory therapies. For example, in a most general case, breathing circuits include an inspiratory limb running from a ventilator to a patient and an expiratory limb running from the patient back to the ventilator.

The ventilator pushes gas through the inspiratory limb to reach the patient. The patient inhales this pushed gas and exhales gas into the expiratory limb. For purposes of the embodiments, any portion of the breathing circuit could be considered a patient circuit or conduit. It should be appreciated that embodiments are well suited to be used in any portion of the patient circuit, any other respiratory gas conduit, and any respiratory component. The term respiratory component refers to any component utilized with the process described in the flow diagrams 800 and 900 of FIGS. 8 and 9, respectively.

If the gas is cold when the patient inhales it, the patient's body works hard to try to warm up the gas for ease of breathing. Humidity can also be added to the circuit, because when someone is intubated for ventilation, the body's natural humidification process is bypassed. In normal breathing, the upper airways heat and humidify inspired gas, and recover heat and humidity from exhaled gas, thereby conserving body heat and water. Due to the intubation (bypassing upper airways), there is a humidity deficit which creates serious physiological problems if not addressed (e.g., through use of a humidified circuit, or heat and moisture exchanger).

When gas is humidified, the temperature in the tube must be kept above the dew point to prevent condensation within the tube. Thus, breathing circuits can be designed with heating wires positioned within the interior of at least the inspiratory limb, or patient circuit.

If a heating wire is positioned within the respiratory gas conduit such that the heating wire stretches the full length of the inspiratory limb, then all of the gas moving through the inspiratory limb becomes heated. Thus, the gas arriving from the inspiratory limb into the patient's airway is also well heated.

One of the challenges associated with providing active humidification to a patient is managing condensation (commonly known in the industry as "rainout") in the patient circuit limbs. Several known approaches to managing condensation include collecting the condensation in known locations (water traps), heating the circuit limbs with a heater wire (heated circuits) and diffusing the water through a porous wall. Heat and humidity from exhaled patient gases can also create condensation in respiratory components in either active or passive humidification therapies and this also presents challenges.

Respiratory circuits can accumulate condensation in a concentrated area that then becomes a site that fosters even greater condensation generation. An example of this phenomena would be a person accidently knocking the circuit, compelling condensation to accumulate at the lowest circuit elevation. This pool of condensation is cooler than the surrounding saturated respiratory gas, facilitating the saturated gas to condense into an even larger pool of condensation, growing with every breath of saturated gas that passes by. The problem can even progress to the point that all the respiratory gases are forced through the liquid, further exacerbating the problem.

As discussed in the application, FLUTED HEATER WIRE, U.S. patent application Ser. No. 13/250,894, the fluted heater wire self-corrects the condensation problem by utilizing grooves. Grooves (or "flutes") are disposed on the heater wire to create a geometry that is conducive to encouraging capillary action.

In one embodiment, at least one groove, as described in the FLUTED HEATER WIRE application, is disposed on a respiratory component coupled with a breathing circuit, wherein the respiratory component is not a fluted heater wire. The surface energy of the respiratory components can be modified with technology common to the art, such as plasma treatment.

The combination of favorable geometry and a high surface energy (low contact angles) will enable the respiratory component to wick up and transport any liquid (e.g. condensation) with which the at least one groove comes in contact. Thus, embodiments provide a device for removing excess condensation from a breathing circuit, or in general, for transporting liquid from a first location to a second location.

Figure 1:
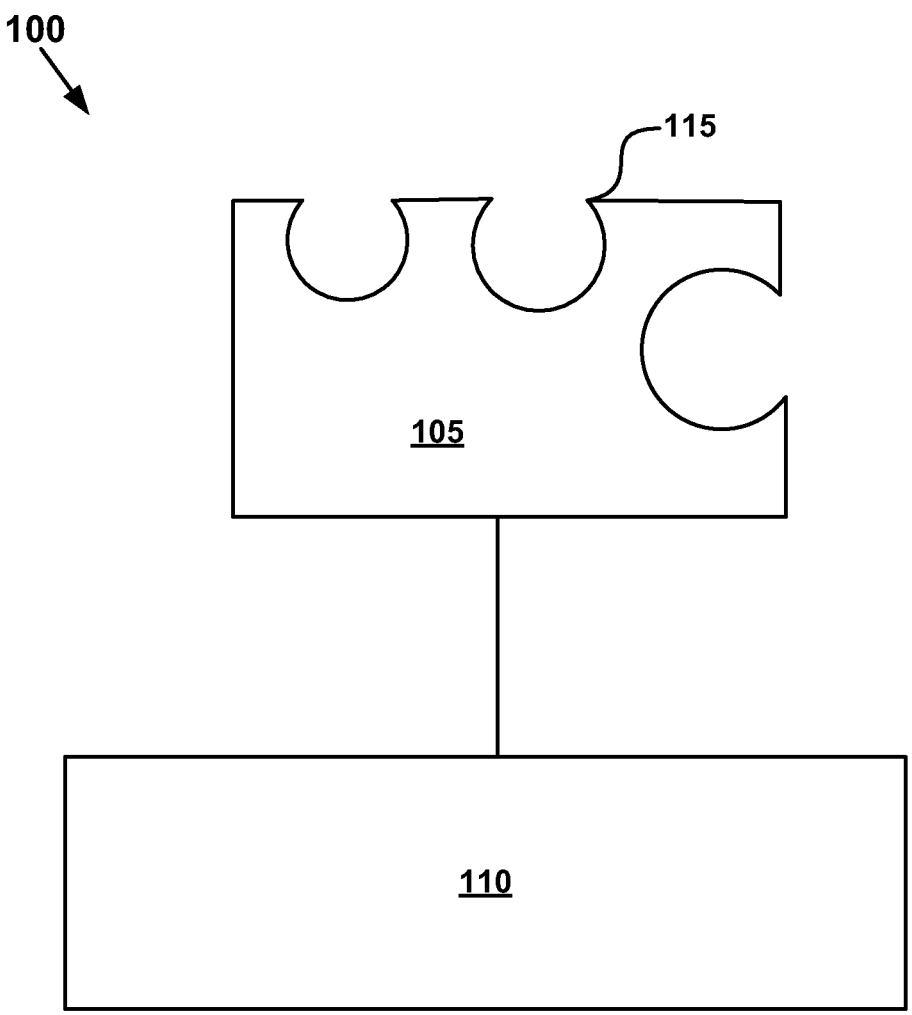
FIG. 1 shows a block diagram of a respiratory component, coupled with a breathing circuit, with at least one groove disposed thereon, in accordance with an embodiment.

FIG. 1 shows a block diagram of a respiratory component 105, coupled with a breathing circuit 110, with at least one groove 115 disposed upon a surface of the respiratory component 105. The at least one groove 115 transports liquid along the surface. In accordance with embodiments, the respiratory component 105 is not a heater wire. In one embodiment, the liquid is water.

Of note, while the at least one groove 115 is shown in FIG. 1, it should be appreciated that there may be more than one groove disposed on the respiratory component 105. Further, it should be appreciated that there are various descriptions of methods for disposing at least one groove 115 on the respiratory component, such as but not limited to, "forming", "molding", "pressing out" and "extruding".

In one embodiment, the at least one groove 115 includes material that is one or more of the following: hydrophilic; antifogging; and antistatic. It should be appreciated that when the material has a hydrophilic character, the combination of the at least one groove 115 and the material more quickly and efficiently wicks the liquid up along the at least one groove 115 and away from the condensation region. In one embodiment, the material is, either partially or wholly, of a material that has an inherently high surface energy.

In one embodiment, the at least one groove 115 includes, but is not limited to, one or more of the following shapes: a V-shape; a square shape; a semi-circular shape; a non-uniform shape; and a combination of the foregoing shapes. As discussed herein, it should be appreciated that there may be any number of grooves disposed on the respiratory component 105. For example, in one embodiment, the grooves are equally spaced across the surface of the respiratory component 105. However, in another embodiment, these grooves are not equally spaced.

Figure 2:
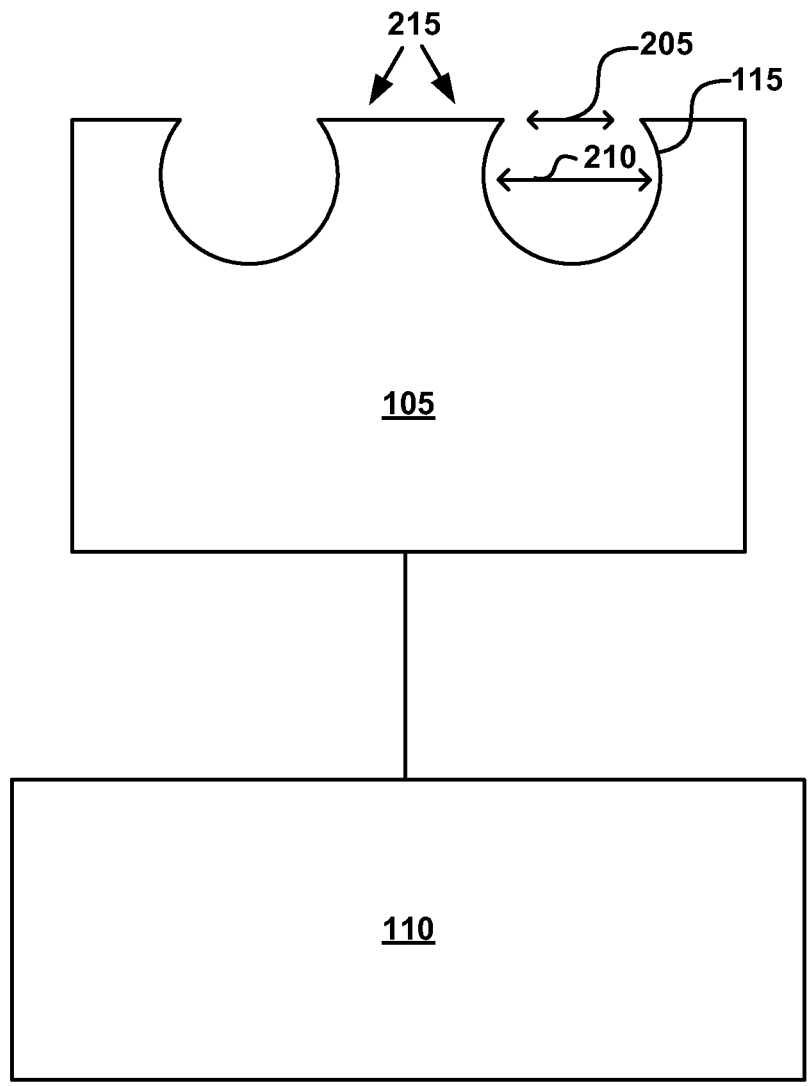
FIG. 2 shows a block diagram of a cross-sectional view of a respiratory component, coupled with a breathing circuit, with at least one groove disposed thereon, in accordance with an embodiment.

FIG. 2 shows a block diagram of a cross-sectional view of a respiratory component, coupled with a breathing circuit, with at least one groove disposed thereon, in accordance with an embodiment. With reference to FIG. 2, it should be appreciated that the geometry of the at least one groove 115 is such that the width of the at least one groove 115 is desired to be as small as possible and the length of the at least one groove 115 is desired to be as big as possible. Further, the contact angle between the at least one groove 115 and the liquid (e.g. water) is desired to be as close to zero as is possible, while still functioning to wick up as much liquid as desired. In other words, the contact angle between the at least one groove 115 and the water is desired to be that of a low contact angle, which is obtained by utilizing a high surface energy. Liquid is thereby caused to be drawn, through capillary action, towards an unwetted part of the at least one groove 115. Moreover, embodiments provide for continuous wicking up of the water from a condensation region.

In one embodiment, the first width 205 of the at least one groove 115 at a surface 215 of the respiratory component 105 is less than a second width 210 of the at least one groove 115. The second width 210 is a maximum width of the at least one groove 115, when viewed in cross-section (as is shown in FIG. 2).

In one embodiment, the evaporation region is a hot surface along the respiratory component 105. For example, the condensation region is considered to be a cooler region, or a place at which the water accumulates and does not evaporate. Once the water is wicked up into the at least one groove 115, the water is transported along the groove away from the condensation region and to a hotter region where the water is able to once again evaporate, or "re-evaporate".

In one embodiment, the surface 215 of the respiratory component 105 is a wall having smooth surface characteristics. In various embodiments, the respiratory component 105 is one or more of the following: a filter; a heat and moisture exchanger; at least one of a filter and a heat and moisture exchanger; a medicament delivery device; a medicament delivery device that is a nebulizer; a gas delivery device, a tubing; an oxygen delivery component; a part of a respiratory mask; a nasal prong component; an endotracheal tube; a tracheostomy device; and surrounded by and not a part of the heater wire (see FIG. 3 and explanation below).

With regards to the filter, in some instances, water pools up around filter components. Embodiments move this pooled liquid away using the at least one groove 115. With regards to the heat and moisture exchanger, the at least one groove 115 is disposed on the surface of the respiratory component 105 such that the surface area for the heat and moisture exchanger is increased. In other instances, liquid can pool up on the patient side of the heat and moisture exchanger. Embodiments move this pooled liquid away using the at least one groove 115. In yet other instances, liquid can pool up in a respiratory mask or endotracheal device or tracheostomy device. Embodiments move this pooled liquid away using the at least one groove 115.

In another embodiment, the respiratory component 105 is at least one of a filter and a heat and moisture exchanger. The respiratory component 105 chemically reacts to received liquid transported from at least one of the filter and the heat and moisture exchanger, in response to a predetermined threshold being detected. For example, once a predetermined value of pooled water is received by the respiratory component 105, the respiratory component 105 reacts chemically to the received liquid. Further, the chemical reaction can serve to provide an alert indicator. The alert indicator sends an alert, prompting something to be adjusted/changed such that the amount of pooled water is lowered. Although this embodiment is described with respect to a heat and moisture exchanger or filter, it should be appreciated that embodiments are well suited to move liquid from other respiratory components to initiate an indication through the reaction of an indicator with the received liquid either by chemical reaction or other mechanism.

As discussed herein, the medicament delivery device is a nebulizer, in one embodiment. Within nebulizers, often times water accumulates through use. In another situation, when water is sprayed within the nebulizer, water is accumulated in caps or other portions. Embodiments enable this pooled water to be transported to another region.

Figure 3:
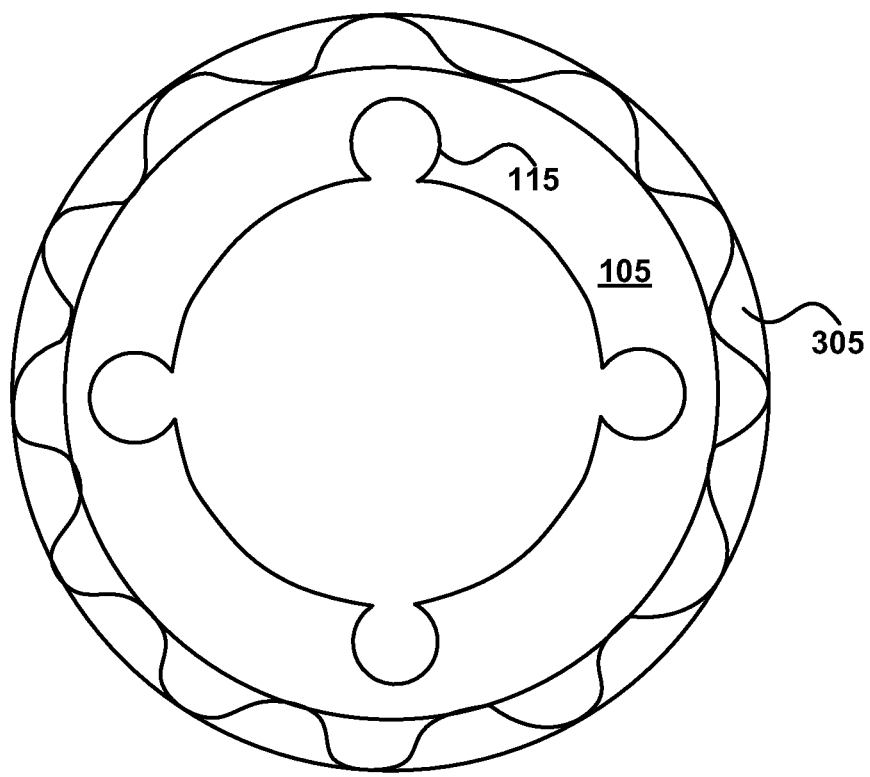
FIG. 3 shows a diagram of a respiratory component surrounded by and not a part of a heater wire, in accordance with an embodiment.

FIG. 3 shows a diagram of the respiratory component 105 surrounded by but not a part of the heater wire 305, in accordance with an embodiment. As can be seen, the respiratory component 105 includes the at least one groove 115 that is disposed in the internal wall surface of the respiratory component 105, while a heated wall or heater wire 305 (for supplying heat) surrounds the respiratory component 105. While in the embodiment and as shown in FIG. 3, the respiratory component 105 is external to and surrounded by the heater wire 305, it should be appreciated that in other embodiments it is not necessary for the heater wire 305 to surround the respiratory component 105.

Figure 4:
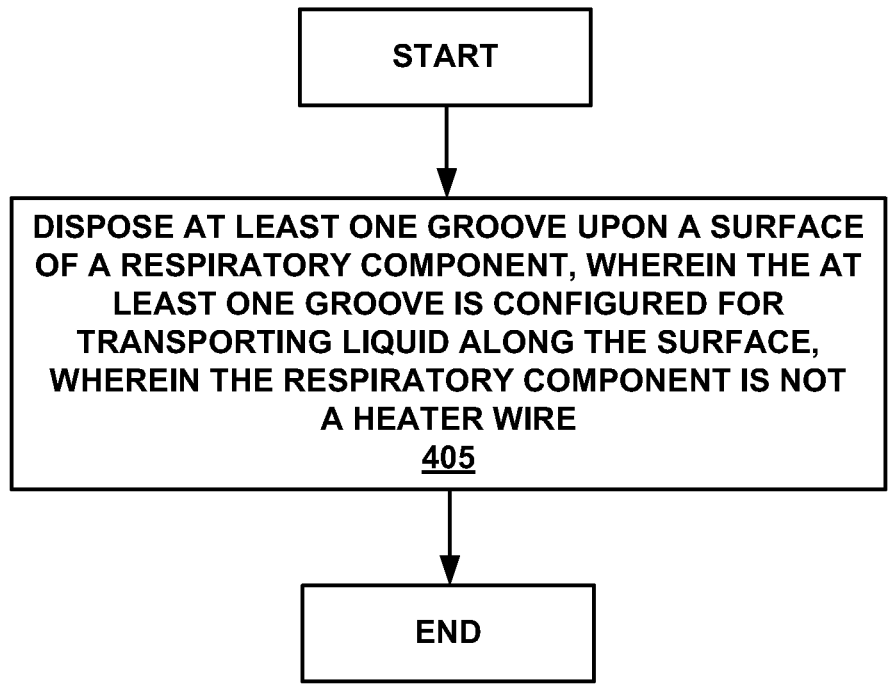
FIG. 4 is a flow diagram of an example method for manufacturing a device for transporting liquid along a surface within a respiratory component, in accordance with an embodiment.

FIG. 4 shows a flow diagram of an example method for manufacturing a device for transporting liquid along a surface within a respiratory component, in accordance with an embodiment.

Referring now to FIGS. 1-4, in one embodiment and as discussed herein at 405 at least one groove 115 is disposed upon a surface 215 of a respiratory component 105, wherein the at least one groove 115 transports liquid along the surface and wherein the respiratory component 105 is not a heater wire.

Figure 5:
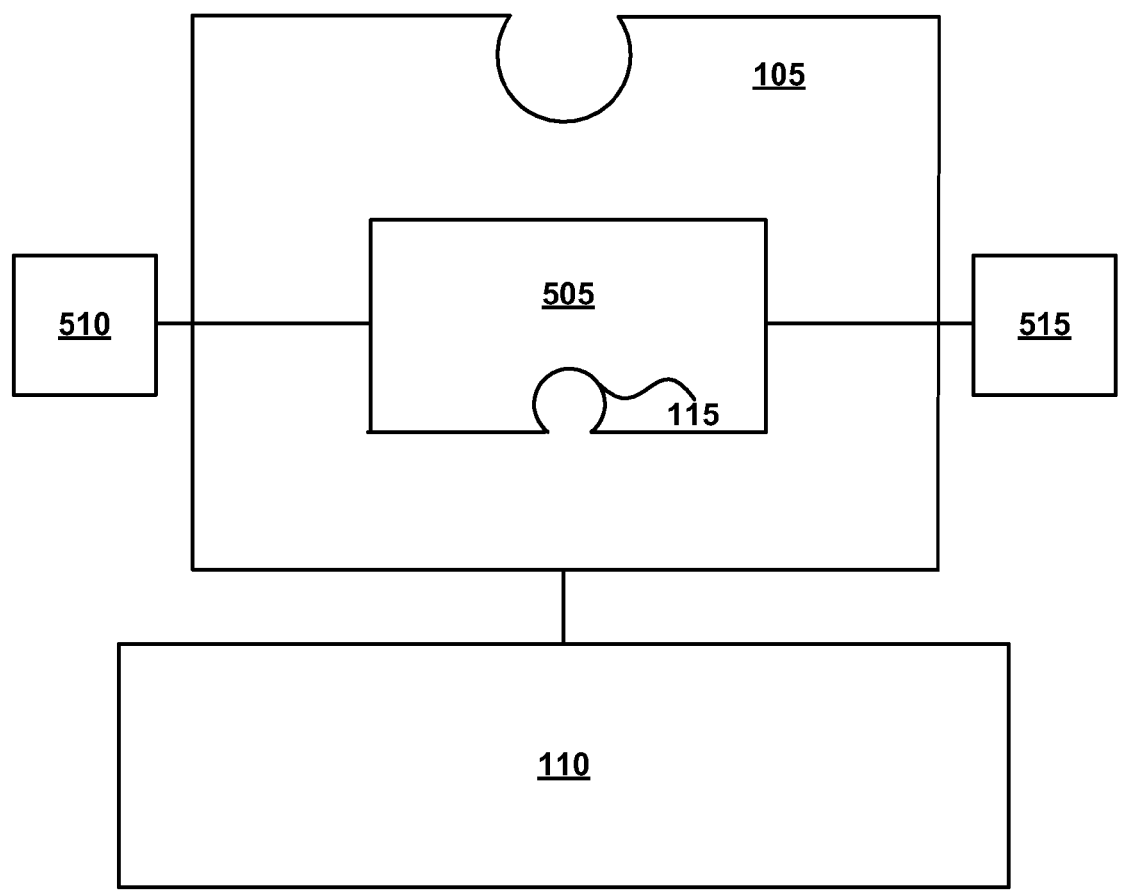
FIG. 5 shows a block diagram of a cross-sectional view of a liquid transporting device, coupled with a breathing circuit, in accordance with an embodiment.

FIG. 5 shows a block diagram of a cross-sectional view of a liquid transporting device 505, coupled with a breathing circuit 110. In one embodiment, the liquid transporting device 505 transports liquid from a first region 510 to a second region 515. The liquid transporting device 505 is disposed on a surface of the respiratory component 105 and is not disposed on a heater wire. In one embodiment, the liquid transporting device 505 is coupled with a breathing circuit 110. In one embodiment, the liquid transporting device 505 includes at least one groove 115 disposed upon the surface of the respiratory component 105. The at least one groove 115 wicks up liquid from the first region 510 and transports the liquid to the second region 515. In one embodiment, the at least one groove 115 evaporates the liquid. The at least one groove may be of a hydrophilic character. In one embodiment, the liquid being wicked up from the first region 510 and transported to the second region 515 is water.

In various embodiments, the surface of the respiratory component 105 may be one or more of the following: a filter component; a heat and moisture exchanger component; a respiratory humidification component; a respiratory medicament delivery component; a respiratory medicament delivery component that is a nebulizer; a respiratory mask; a nasal prong component; an endotracheal tube; a tracheostomy device; and an oxygen delivery component.

In another embodiment, the first region 510 is a region of condensation. In yet another embodiment, the second region 515 is a region for evaporation of the liquid. In one embodiment, the second region 515 includes an indicator that is activated by the liquid transported from the first region 510. In one embodiment, the indicator is activated by a chemical reaction with the liquid.

In one embodiment, the liquid transporting device 505 includes a porous material that wicks up liquid (e.g. water) on a first surface and releases the liquid on a second surface that faces away from the first surface. It should be appreciated that the grooves discussed herein with regards to FIGS. 1-4 may be integrated with the liquid transporting device 505 of FIG. 5.

Thus, embodiments enable liquid (e.g. water) to be transported to desired regions and/or removing excess condensation from a region. It should be appreciated that liquid may be a liquid other than water. For example, other transported liquid may be, but is not limited to being, medicaments, secretions, or any other liquid of therapeutic or functional value to the patient or respiratory system.

All statements herein reciting principles, aspects, and embodiments of the technology as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present technology, therefore, is not intended to be limited to the embodiments shown and described herein. Rather, the scope and spirit of present technology is embodied by the appended claims.

What is claimed is:

1. A respiratory component comprising:
   grooves configured for transporting a liquid from a first region to a second region, wherein all of said grooves are disposed in an internal wall surface of said respiratory component and are not disposed on a heater wire, each groove having a semi-circular cross-section and a first cross-sectional width at said internal wall surface that is less than a second cross-sectional width of said groove, said second cross-sectional width being a maximum cross-sectional width of said groove,
   wherein said respiratory component and all of said grooves, when viewed in a cross section, are (i) covered by an outer layer comprising said heater wire and (ii) continuously surrounded by the heater wire, such that said internal wall surface and grooves are radially inward of, and separated from, said outer layer comprising said heater wire.

2. The respiratory component of claim 1, wherein said grooves are configured for wicking up liquid from said first region and transporting said liquid to said second region.

3. The respiratory component of claim 1, wherein said grooves are configured for evaporation of said liquid.

4. The respiratory component of claim 1, wherein said grooves comprise a surface with a hydrophilic character.

5. The respiratory component of claim 1, wherein said first region is a region of condensation.

6. The respiratory component of claim 1, wherein said second region is a region configured for evaporation of said liquid.

7. The respiratory component of claim 1, wherein said respiratory component comprises a liquid transporting device comprising a porous material configured for wicking up liquid.

8. A respiratory component coupled with a breathing circuit, said respiratory component comprising: a tube having an internal wall surface comprising grooves that extend longitudinally along the internal wall surface, each groove having a semi-circular cross-section and a first cross-sectional width at the internal wall surface that is less than a second cross-sectional width of the groove, said second cross-sectional width being a maximum cross-sectional width of said groove, wherein the tube, when viewed in cross section, is (i) covered by an outer layer comprising a heater wire and (ii) continuously surrounded by the heater wire, such that said internal wall surface and grooves are radially inward of, and separated from, said outer layer comprising said heater wire.

9. The respiratory component of claim 8, wherein the grooves are further configured for transporting said liquid from a condensation region to a heated region for evaporation.

10. The respiratory component of claim 8, wherein said surface of the internal wall comprises smooth surface characteristics.

11. The respiratory component of claim 8, wherein said respiratory component comprises a filter.

12. The respiratory component of claim 8, wherein said respiratory component comprises a heat and moisture exchanger.

13. The respiratory component of claim 8, wherein said respiratory component comprises a medicament delivery device.

14. The respiratory component of claim 13, wherein said medicament delivery device is a nebulizer.

15. The respiratory component of claim 8, wherein said respiratory component is part of a gas delivery device.

16. The respiratory component of claim 8, wherein said respiratory component is an oxygen delivery component.

17. The respiratory component of claim 8, wherein said respiratory component is a respiratory mask.

18. The respiratory component of claim 8, wherein said respiratory component is a nasal prong component.

19. The respiratory component of claim 8, wherein said respiratory component is an endotracheal device.

20. The respiratory component of claim 8, wherein said respiratory component is a tracheostomy device.

21. The respiratory component of claim 8, wherein a surface of said grooves comprises a hydrophilic component.

22. The respiratory component of claim 8, wherein the maximum cross-sectional width of the groove is less than a maximum cross-sectional dimension of the lumen.

* * * * *